United States Patent
Deo et al.

(10) Patent No.: US 7,825,257 B1
(45) Date of Patent: Nov. 2, 2010

(54) SYNTHESIS OF BENZOTRIAZOLE MONOMER

(75) Inventors: Keshav Deo, Baroda (IN); Chandrakant Chunilal Shah, Baroda (IN); Kalpesh Patel, Kheda (IN); Nilpesh Patel, Baroda (IN); Viral Parekh, Morbi (IN); Ronak Patel, Ahmedabad (IN); Jignesh Soni, Patan (IN); Hiral Shah, Baroda (IN); David E. Seelye, Williamsville, NY (US); Mahendra P. Nandu, Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 15 days.

(21) Appl. No.: 12/253,351

(22) Filed: Oct. 17, 2008

Related U.S. Application Data

(60) Provisional application No. 60/981,837, filed on Oct. 23, 2007.

(51) Int. Cl.
 *C07D 249/20* (2006.01)
(52) U.S. Cl. ...................................... 548/259; 548/260
(58) Field of Classification Search .................. 548/257, 548/259, 260
 See application file for complete search history.

(56) References Cited

U.S. PATENT DOCUMENTS

| 3,213,058 A | 10/1965 | Boyle et al. |
| 4,528,311 A | 7/1985 | Beard et al. |
| 4,716,234 A | 12/1987 | Dunks et al. |
| 4,803,234 A | 2/1989 | Cantatore et al. |

*Primary Examiner*—Kamal A Saeed
*Assistant Examiner*—Kristin Bianchi
(74) *Attorney, Agent, or Firm*—Joseph Barrera

(57) ABSTRACT

The synthesis of benzotriazole monomers and the use of the benzotriazole monomers and one or more other monomers to prepare ultraviolet (UV) light absorbing polymer compositions. The synthetic methods described in this application provide a significant improvement over the previous methods used to prepare benzotriazole monomers.

6 Claims, No Drawings

SYNTHESIS OF BENZOTRIAZOLE MONOMER

CROSS REFERENCE

This application claims the benefit of Provisional Patent Application No. 60/981,837 filed Oct. 23, 2007 which is incorporated by reference herein.

FIELD OF THE INVENTION

This invention relates to the synthesis of benzotriazole monomers and the use of the benzotriazole monomers with one or more other monomers to prepare ultraviolet (UV) light absorbing polymer compositions. Ocular devices, particularly intraocular lenses and contact lenses are prepared from such ultraviolet light absorbing polymer compositions.

BACKGROUND OF THE INVENTION

U.S. Pat. No. 3,213,058, to Boyle et al., discloses benzotriazole compounds and their incorporation into certain plastics as UV absorbers, via reaction with carboxy and hydroxy groups contained in said compounds.

U.S. Pat. No. 4,528,311 discloses benzotriazole monomers which are copolymerizable with vinyl monomers such as methyl methacrylate to yield optically clear polymers useful in the preparation of intraocular and contact lenses. One of the disclosed benzotriazole monomers and is 2-[3'-t-butyl-2'-hydroxy-5'-(3"-methacryloxypropyl)phenyl]-5-chlorobenzotriazole as shown in Scheme A below:

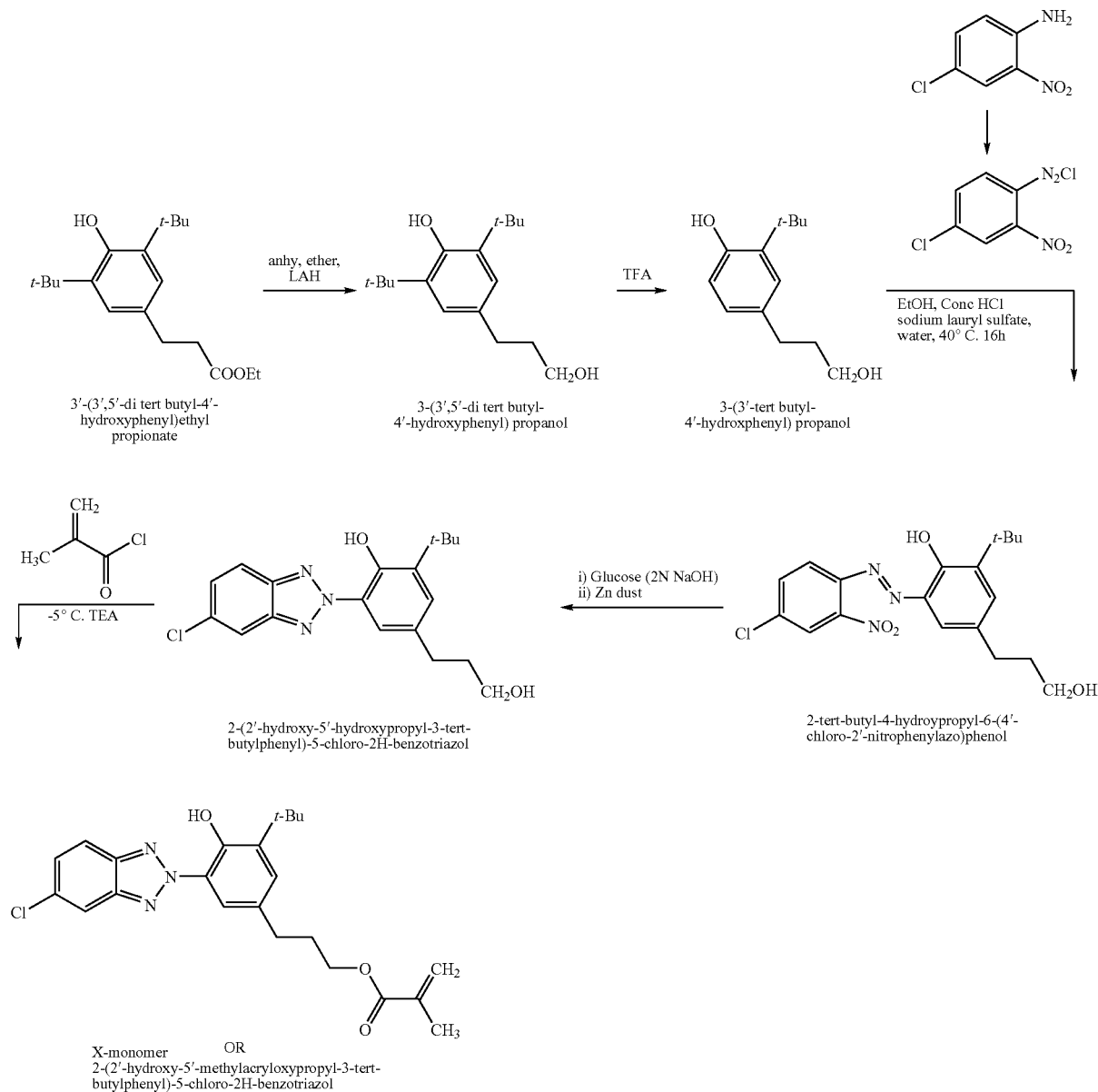

U.S. Pat. No. 4,803,234 describes a process for the preparation of another benzotriazole monomer, 2-[3'-tert-butyl-5'-(3"-dimethylvinylsilylpropoxy)2'-hydroxypheynyl]-5-methoxybenzotriazol, which is as shown in the scheme B below.

Scheme B

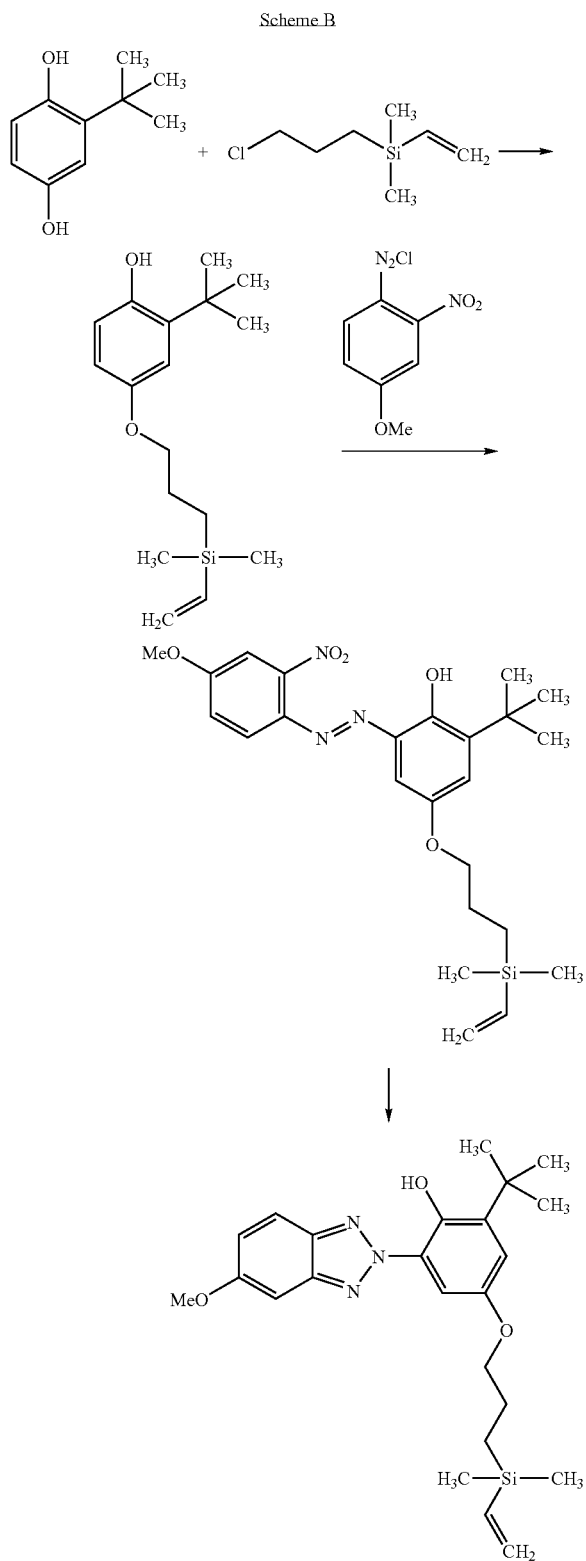

U.S. Pat. No. 4,716,234 describes other benzotriazole monomers illustrative of which are 2-[2'-hydroxy-5'-(β-methacryloxyethoxy)-3'-tert-butylphenyl]-5-methoxy-2H-benzotriazole:

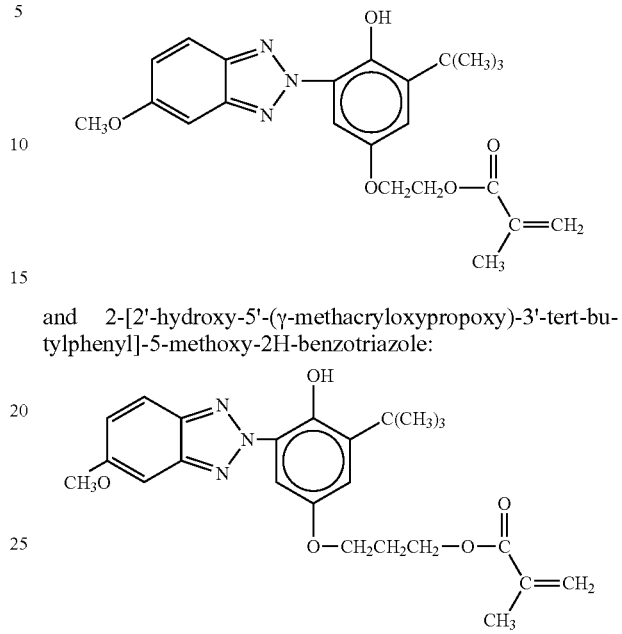

and 2-[2'-hydroxy-5'-(γ-methacryloxypropoxy)-3'-tert-butylphenyl]-5-methoxy-2H-benzotriazole:

The synthetic schemes for producing benzotriazole monomers suffer from difficulty in obtaining the starting materials and are expensive to carry out.

SUMMARY OF THE INVENTION

This invention relates to the synthesis of benzotriazole monomers and the use of the benzotriazole monomers and one or more other monomers to prepare ultraviolet (UV) light absorbing polymer compositions. The synthetic methods described below provide a significant improvement over the previous methods used to prepare benzotriazole monomers.

Ocular devices, particularly intraocular lenses and contact lenses are prepared from such ultraviolet light absorbing polymer compositions. The polymerization of the benzotriazole monomers with acrylic monomers, particularly aromatic acrylic monomers, can provide significant functional advantages such as polymer materials with a relatively high refractive index for optical power and sufficient flexibility and strength for insertion of an intraocular lens.

DETAILED DESCRIPTION OF THE INVENTION

The invention pertains to improvements in producing benzotriazole monomers relative to the methods depicted in Schemes A and B, above.

In one embodiment, the invention is directed to a method of preparing a benzotriazole monomer, the method comprising:
a) providing a compound (A):

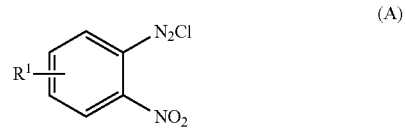

(A)

where $R^1$ is H, a halogen atom, alkyl or alkoxy;

b) providing a compound (B):

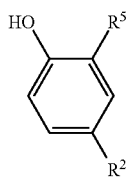
(B)

where $R^2$ is $OR^6$, $OR^6OH$ or $R^6OH$, $R^5$ is H, or a straight or branched alkyl of 1-6 carbon atoms, R is an organic leaving group and $R^6$ is a divalent hydrocarbon group;

c) reacting the compounds (A) and (B) under alkaline conditions to produce a diazo compound (C):

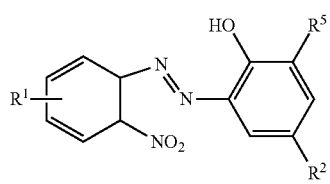
(C)

d) forming a compound (D) from the compound (C):

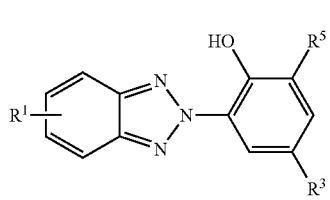
(D)

where $R^3$ is OH, $OR^6OH$ or $R^6OH$; and then, e) reacting the compound (D) with an alkyl halide substituted with a group comprising a polymerizable C=C double bond, or with a carboxylic acid halide or anhydride comprising polymerizable C=C double bond, to produce a compound of the formula (E):

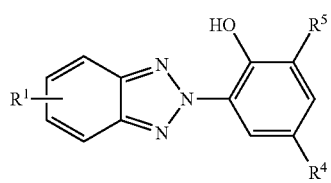
(E)

where $R^4$ is a group comprising a polymerizable C=C double bond, and a linking moiety comprising an ester and/or ether group.

In other aspects the invention pertains to a method of preparing a monomer of formula (E), the method comprising:

a) preparing a compound (F):

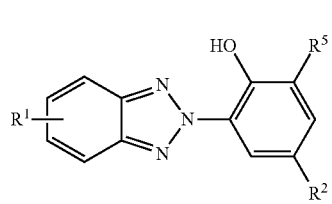
(F)

where $R^1$ and $R^5$ are as previously defined, $R^2$ is OR, and R is organic leaving group;

b) deprotecting the $R^2$ group of the compound (F) to produce a compound (D):

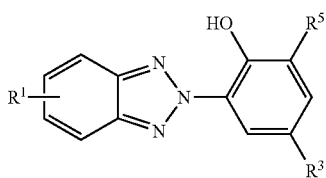
(D)

where $R^3$ is OH; and then c) reacting the compound (D) with an alkyl halide substituted with a group comprising a polymerizable C=C double bond or a carboxylic acid halide or anhydride having polymerizable C=C double bond thereon to produce a compound (E).

In other aspects the invention pertains to a method of preparing a monomer of formula (E), the method comprising:

a) providing a compound (A):

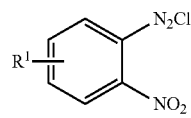
(A)

where $R^1$ is as previously defined b) providing a compound (B):

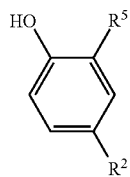
(B)

where $R^5$ is as previously defined, $R^2$ is $R^6OH$ and $R^6$ is a divalent hydrocarbon group;

c) reacting the compounds (A) and (B) to produce a diazo compound (C):

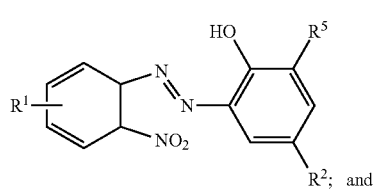
(C)

d) producing said monomer (E) from the compound (C), wherein:
the step b) comprises reducing the carboxylic acid group of a compound of the formula (G):

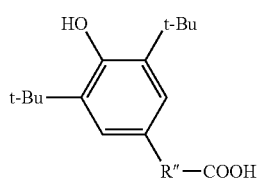
(G)

wherein R" is a divalent hydrocarbon or oxyhydrocarbon group, to provide a compound of the formula (H):

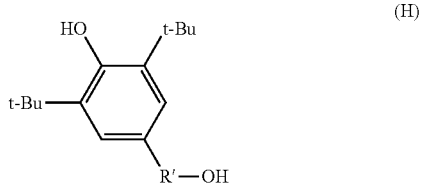

where R' is R"CH$_2$; and then dealkylating the reduction product (H) to produce a compound (B).

In still further aspects the invention pertains to a method of preparing a benzotriazole monomer of formula (E) where R$^4$ is a group comprising a polymerizable C═C double bond, and a linking moiety comprising an ester group, the method comprising:

a) providing a compound (A):

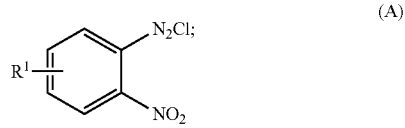

b) providing a compound (B):

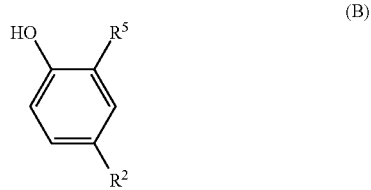

where R$^2$ is OR$^6$OH or R$^6$OH, R$^5$ is H, or a straight or branched alkyl of 1-6 carbon atoms, R is an organic leaving group and R$^6$ is a divalent hydrocarbon group;

c) reacting the compounds (A) and (B) to produce a diazo compound (C):

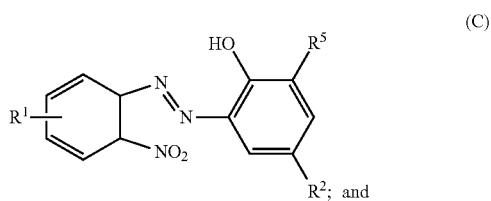

then d) producing said monomer (E) from the compound (C), wherein:

in said step c) the compounds (A) and (B) are reacted under alkaline conditions.

Further aspects are provided in the detailed description and claims that follow.

In the formulas above, R$^1$ is H, a halogen atom, alkyl or alkoxy. In particular examples R' can be a hydrogen atom, a chloro group, a methyl group, a methoxy or an ethoxy group.

R$^2$ is OR, OR$^6$OH or R$^6$OH. R is an organic leaving group. R should be a group that is stable under alkaline conditions but that can be removed to provide an OH group by a suitable reaction, for instance an alkaryl group that is optionally substituted on the aromatic ring, such as benzyl, methylbenzyl or phenylethyl, a tetrahydropyranyl group that is optionally substituted on the pyrane ring or a t-butyldimethysilyl group. R$^6$ is a divalent hydrocarbon group for instance a C$_1$-C$_{10}$ alkylene group, which can be straight or branched.

R$^5$ is H, or a straight or branched alkyl of 1-6 carbon atoms. In some embodiments R$^5$ is a tertiary alkyl such as t-butyl.

R$^3$ is OH, OR$^6$OH or R$^6$OH, where R$^6$ is as previously defined.

R$^4$ is a group comprising a polymerizable C═C double bond, and a linking moiety comprising an ester and/or ether group, obtained by reaction of an R$^3$ group with a suitable etherifying or etherifying agent having a polymerizable C═C double bond. The etherifying agent can be: an alkyl halide substituted with a group comprising a polymerizable C═C double bond, for instance an alkyl iodide having polymerizable C═C double bond. The etherifying agent can be a compound of the formula X—R$^7$—R$^8$ where X is a labile halogen atom, for instance iodo, R$^7$ is alkylene and R$^8$ is a silyl group having a vinyl group attached to the silicon atom thereof, for instance compounds of the formula I—R$^7$Si(R$^9$)$_2$CH═CH$_2$, where R$^7$ is alkylene, for instance methylene, ethylene, propylene or butylene, and the R$^9$ groups are the same or different monovalent hydrocarbon groups, such as methyl, ethyl or phenyl groups. The esterifying agent having a polymerizable C═C double bond can be for instance methacryloyl chloride, acryloyl chloride, methacrylic anhydride and acrylic anhydride.

R" is a divalent hydrocarbon group or oxyhydrocarbon group, particularly alkylene or oxyalkylene having 1 to 10 carbon atoms. R' is R"CH$_2$.

Some aspects of the invention are illustrated in connection with a process for preparing 2-[2'-hydroxy-5'-methacryloxypropyl)-3'-tert-butylphenyl)-5-chloro-2H-benzotriazole, which has the formula (I) below:

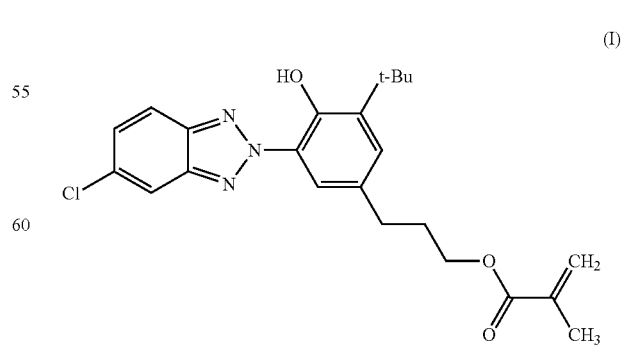

An inventive process for production of (I) is given below in the synthetic Scheme C below:

lithium aluminum hydride (LAH). The process step is easy to handle and is feasible on commercial scale.

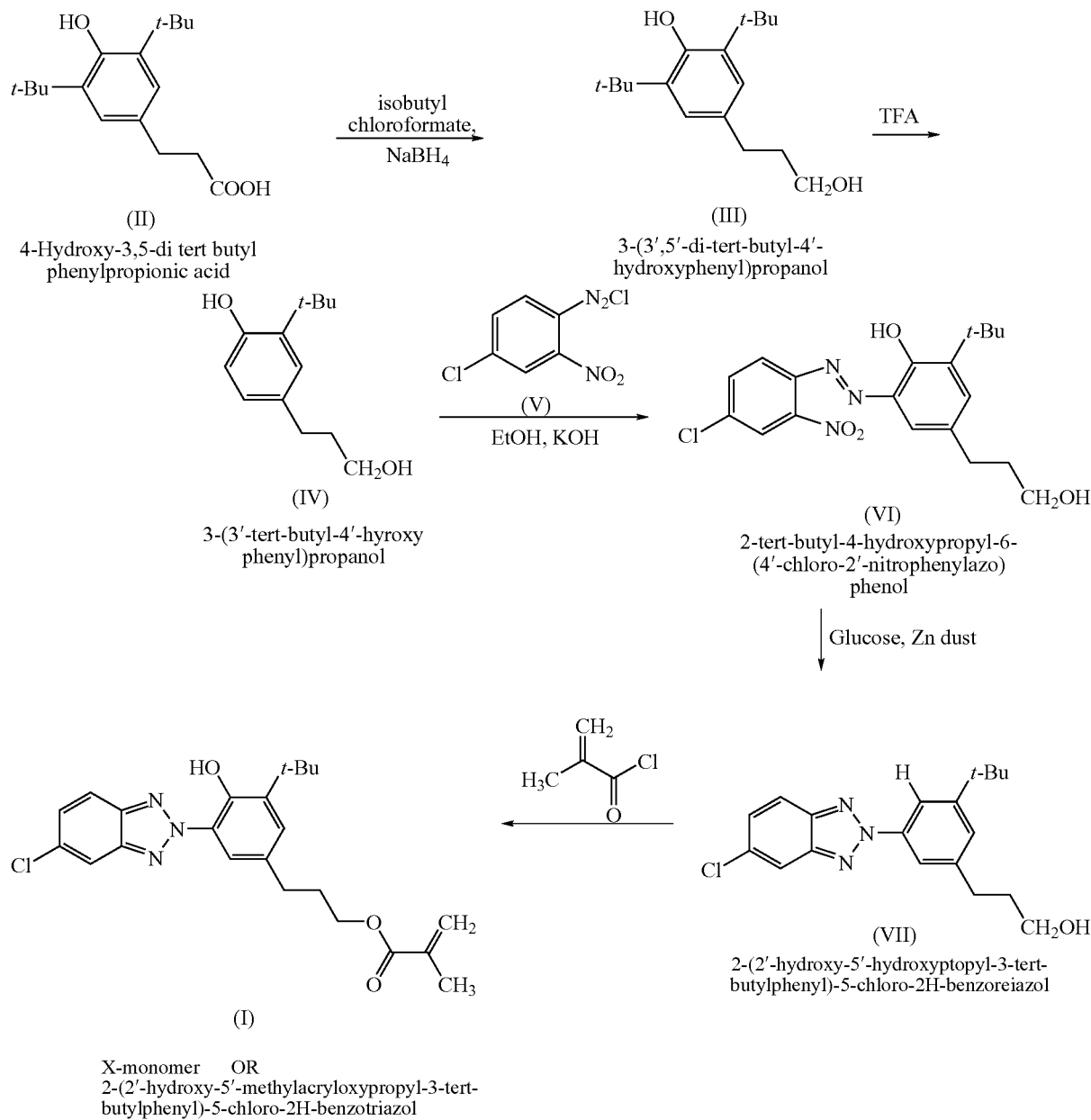

Advantages of the process as shown above, compared to that in Scheme A include the following:
a) The starting material acid (II) used in the process of present invention is inexpensive and commercially available.
b) The process of present invention need not convert acid the (II) to ester as used in Scheme A, above, a cost saving and simplification.
c) The acid (II) is converted to alcohol (III) by using inexpensive and commercially available reagents like isobutyl chloroformate and sodium borohydride. This process avoids the use of critical and hazardous reagents such as d) The compound (III) and (IV) obtained after each process step can be used as such for the next step without purification.
e) The third step, condensation of (IV) and (V) is performed in basic media opposed to acidic media as mentioned in U.S. Pat. No. 4,528,311. As a result, compound (VI) is obtained in higher yields and greater purity.
f) The inventive process requires less amounts of ethanol compared to the prior art process given in U.S. Pat. No. 4,528,311.

g) The triazole (VII) is prepared in-situ from (IV) without isolation of an azodye as required of scheme A.

h) Compound (VII) can be purified by filtration through a silicagel column resulting in higher purity, and compound (I) also can be purified by filtration through silicagel column followed by crystallization from methanol. The purity of final compound (I) obtained by the process of present invention is from 97% to 99% by HPLC.

Other aspects the invention are illustrated in connection with a process for preparing 2-[3'-tert-butyl-5'-(3"-dimethylvinylsilylpropoxy)2'-hydroxypheynyl]-5-methoxybenzotriazol. A reaction scheme for preparing this monomer in accordance with the invention is shown in Scheme D below:

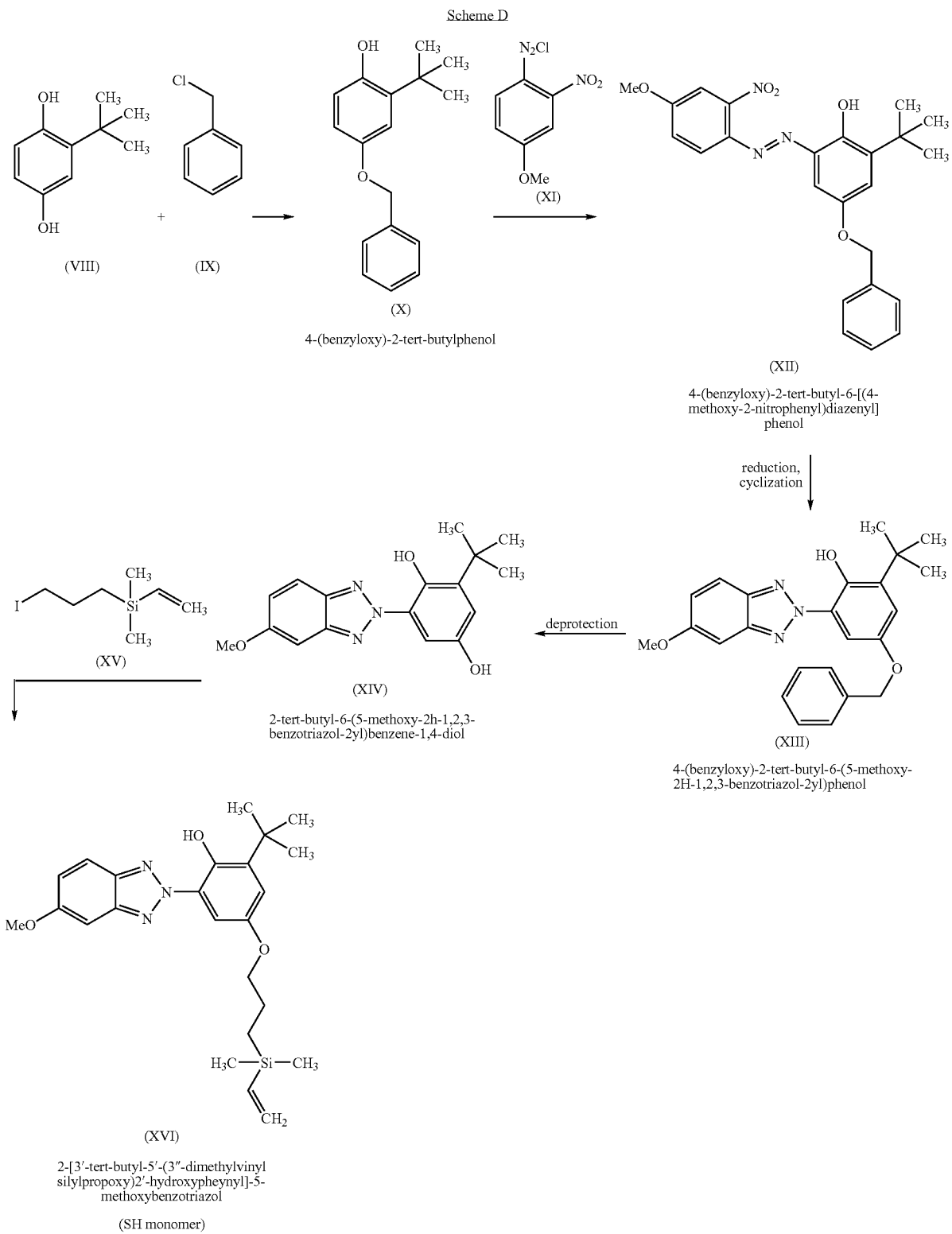

Advantages of the process as shown Scheme D, compared to that in Scheme B above include the following:
a) The iodopropyldimethylvinylsilane is used in the final step which effectively minimize the loss of the compound occurred during earlier steps if iodopropyldimethylvinylsilane condensed in the beginning.
b) The azo dye (XII) is of higher purity which in turn increases the yield of the reductive cyclization step.
c) The benzyl group is a more preferred protecting group over other groups such as THP (tetrahydropyranyl) or TBDMS (t-butyldimethylsilyl).
d) The overall yield to the desired benzotriazole of Scheme D is greater than that of Scheme A or Scheme B.

The benzotriazole monomer compounds are useful in preparing lens polymers capable of blocking UV light. For application as an intraocular lens, polymeric materials are prepared with select lens monomer(s). The resulting polymers are of sufficient optical clarity and will have a relatively high refractive index of approximately 1.40 or greater.

An exemplary listing of lens monomers include: $C_1$-$C_{10}$ alkyl methacrylates (e.g., methyl methacrylate, ethyl methacrylate, propyl methacrylate, butyl methacrylate, octyl methacrylate, or 2-ethylhexyl methacrylate; $C_1$-$C_{10}$ alkyl acrylates (e.g., methyl acrylate, ethyl acrylate, propyl acrylate, n-butyl acrylate, n-hexyl acrylate, 2-ethylhexyl acrylate or 2-ethoxyethyl acrylate; $C_6$-$C_{40}$ arylalkyl acrylates (e.g., 2-phenylethyl acrylate, 2-phenoxyethyl acrylate, 2-phenoxyethyl methacrylate, benzyl acrylate, 3-phenylpropyl acrylate, 4-phenylbutyl acrylate, 5-phenylpentyl acrylate, 8-phenyloctyl acrylate, or 2-phenylethoxy acrylate; and $C_6$-$C_{40}$ arylalkyl methacrylates (e.g., 2-phenylethyl methacrylate, 3-phenylpropyl methacrylate, 4-phenylbutyl methacrylate, 5-phenylpentyl methacrylate, 8-phenyloctyl methacrylate, 2-phenoxyethyl methacrylate, 3,3-diphenylpropyl methacrylate, 2-(1-naphthylethyl)methacrylate, benzyl methacrylate, or 2-(2-naphthylethyl)methacrylate.

Alternatively, the $C_6$-$C_{40}$ arylalkyl acrylates can be defined by the following formula:

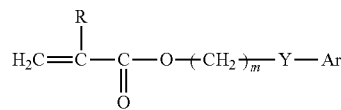

wherein: R is H or $CH_3$; m is 0-10;
Y is nothing, O, S, or NR wherein R is H, $CH_3$ or another lower alkyl, iso-$OC_3H_7$, phenyl or benzyl;
Ar is any aromatic ring, e.g., phenyl, which can be unsubstituted or substituted with H, $CH_3$, $C_2H_5$, n-$C_3H_7$, iso-$C_3H_7$, $OCH_3$, $C_6H_{11}$, Cl, Br or OH.

Reinforced cross-linked silicone elastomers can be prepared by polymerizing silicon elastomers with siloxane polymer containing 12 to 18 mol percent of aryl substituted siloxane units of the formula $R^4R^5$—SiO. In the formula, $R^4$ and $R^5$ are the same or different and represent phenyl, mono-lower alkyl substituted phenyl groups, or di-lower alkyl substituted phenyl groups. Preferably both $R^4$ and $R^5$ are phenyl. The siloxane polymer will have end blockers containing siloxane units of the formula $R^1R^2R^3$—$SiO_5$ wherein $R^1$ and $R^2$ are alkyl, aryl or substituted alkyl or substituted aryl groups, and $R^1$ and $R^2$ can be the same or different. The $R^3$ group of the end blocking siloxane units is an alkenyl group. Preferably, the end blocker is a dimethylvinyl siloxane unit.

The balance of the polymer consists of dialkyl siloxane units of the formula $R^6R^7$—SiO wherein $R^6$ and $R^7$ are the same or different from and are methyl or ethyl groups, and the polymer has a degree of polymerization from 100 to 2000. Preferably, $R^6$ and $R^7$ are both methyl, and the degree of polymerization is approximately 250.

A trimethyl silyl treated silica reinforcer is finely dispersed in the polymer, in a weight ratio of approximately 15 to 45 parts of the reinforcer to 100 parts of the polymer. Preferably, there is approximately 27 parts of reinforcer to 100 parts of the copolymer.

Polymeric materials prepared can be prepared by polymerizing the following monomeric components:
5% to 25% by weight of acrylate represented by the general formula

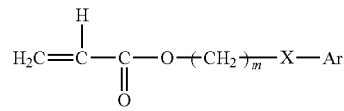

wherein Ar represents an aromatic ring of which hydrogen atom may be substituted by a substitutional group, X represents an oxygen atom or a direct bonding, and m represents an integer from 1 to 5;

(B) 50% to 90% by weight of 2-hydroxyethyl(meth)acrylate; and (C) 5% to 45% by weight of a (meth)acrylate monomer though not of the formula that represent monomer (A) and not 2-hydroxyethyl(meth)acrylate. Also, the coefficient of water absorption of the homopolymer of monomer (C) is not more than 30% by weight. The coefficient of water absorption ($H_2O_{abs.}$ %) is defined as the following equation: $H_2O_{abs.}$ %=$[(W_h-W_d)/W_d] \times 100$ wherein the value is calculated at 25° C. by using a sample 1 mm thick; $W_h$ represents a weight (g) of the sample in an equilibrium state with water, and $W_d$ represents a weight (g) of the sample in a dry state. The water content (% Water) is given by the following formula:

$$\%\text{Water}=[(W_h-W_d)/W_h] \times 100$$

An exemplary listing of (meth)acrylate monomer (C) include an alkyl (meth)acrylate containing a straight chain, a branched chain or cyclic chain such as methyl(meth)acrylate, ethyl(meth)acrylate, propyl(meth)acrylate, butyl(meth)acrylate, pentyl(meth)acrylate, hexyl(meth)acrylate, heptyl (meth)acrylate, nonyl(meth)acrylate, stearyl meth)acrylate, octyl(meth)acrylate, decyl(meth)acrylate, lauryl(meth)acrylate, pentadecyl(meth)acrylate, 2-ethylhexyl(meth)acrylate, cyclopentyl(meth)acrylate, (meth)acrylate, cyclohexyl (meth)acrylate: an alkyl(meth)acrylate containing 1 to 5 carbon atoms of alkyl group: a hydroxyalkyl(meth)acrylate containing a straight chain, a branched chain or cyclic chain, except for 2-HE(M)A (B), and any mixture thereof. Among the alkyl methacrylates those containing 1 to 3 carbon atoms of alkyl group are preferred. Among the hydroxyalkyl methacrylates those containing 3 to 6 carbon atoms of hydroxyalkyl group are preferred.

Polymeric materials can be prepared by copolymerizing a specific monomer mixture comprising perfluorooctylethyloxypropylene (meth)acrylate, 2-phenylethyl (meth)acrylate, and an alkyl(meth)acrylate monomer having the following general formula,

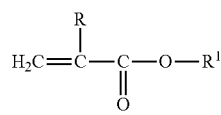

wherein R is hydrogen or methyl and $R^1$ is a linear or branched $C_4$-$C_{12}$ alkyl group. The perfluorooctylethyloxypropylene (meth)acrylate is present from 5% to 20% by weight, the 2-phenylethyl(meth)acrylate is present from 40% to 60% by weight, the alkyl(meth)acrylate monomer is present from 30% to 50% by weight and the crosslinking agent is present from 0.5% to 4% by weight.

The above described polymeric materials are prepared by generally conventional polymerization methods from the respective monomeric components. A polymerization mixture of the monomers in the selected amounts is prepared. To this mixture is added at least one other crosslink agent particularly suited for an acrylate-methacrylate- or acrylamide-based monomer and a conventional thermal free-radical initiator. The mixture is introduced into a mold of suitable shape to form the optical material and the polymerization initiated by gentle heating. Typical thermal, free radical initiators include peroxides, such as benzophenone peroxide, peroxycarbonates, such as bis-(4-t-butulcyclohexyl)peroxydicarbonate, azonitriles, such as azobisisobytyronitrile, and the like. A preferred initiator is bis-(4-t-butylcyclohexyl)peroxydicarbonate (PERK).

Alternatively, the monomers can be photopolymerized by using a mold which is transparent to actinic radiation of a wavelength capable of initiating polymerization of these acrylic monomers and crosslink agents. Conventional photoinitiator compounds, e.g., a benzophenone-type photoinitiator, can be introduced to facilitate the photopolymerization.

Although the invention can be embodied as many different compositions as described above, the compositions described is an exemplification of the principles of the invention and is not intended to limit the invention to the particular embodiments illustrated.

Various aspects of the invention are illustrated in the Examples below:

Example 1

Preparation of 3-(3',5'-di-tert-butyl-4'-hydroxyphenyl)propanol (III)

To a stirred solution of 4-Hydroxy-3,5-di-tertbutylphenyl propionic acid (5.0 Kg) in THF (25.0 L) was added triethylamine (4.5 L). The reaction mixture was cooled up to 0° C.

Isobutyl chloroformate (3.0 L) was added dropwise and stirred at 0° C. for 2 hr. Reaction mixture was filtered. The residue was washed with tetrahydrofuran (5.0 L). Both of the filtrates were combined and slowly a solution of sodium borohydride (2.5 Kg) in DM Water (10.0 L) was added over 5-6 hr and then the mixture stirred at 0° C. for 2 hr. The reaction mixture was acidified with 1M aq. HCl (approx. 10.0 L) to bring the mixture to pH 2. The reaction mixture was extracted twice with ethyl acetate (15.0 L). The organic layers was combined, washed with water (10.0 L), brine (10.0 L) and evaporated to dryness at reduced pressure to give the title compound (5.0 Kg).

Crude yield: 100%; Purity: 65% by HPLC

Example 2

Preparation of 3-(3'-tert-butyl-4'-hydroxyphenyl)propanol (IV)

A stirred solution of III (12.5 Kg) in trifluoroacetic acid (60.0 L) was heated 40° C. for 6 hrs. After completion of reaction on TLC, reaction mixture was quenched in ice-water and extracted 3 times with dichloromethane (25.0 L). Total organic layers were combined and evaporated to dryness at atmospheric pressure. A solution of sodium hydroxide (3.0 Kg) in methanol (50.0 L) was added to the residue and stirred at room temperature for 1 hr. The solution was neutralized with 1N HCl and extracted 3 times with dichloromethane (25.0 L). All the organic layers were combined and washed with saturated sodium carbonate solution (10.0 L), DM Water (10.0 L), brine (10.0 L) and evaporated to dryness under reduced pressure to give the title compound (7.5 Kg)

Crude yield: 76%; Purity: 63% by HPLC

Example 3

Preparation of 2-tert-butyl-4-hydroxypropyl-6-(4'-chloro-2'-nitrophenylazo) phenol (VI) and 2-(2'-hydroxy-5'-hydroxypropyl-3-tert-butylphenyl)-5-chloro-2H-benzotriazol (VII)

(i) Preparation of Diazonium Salt:

A stirred solution 4-chloro-2-nitroaniline (0.86 Kg) in conc. $H_2SO_4$ (1.7 L) was poured in to crushed-ice, filtered and washed with water to remove acidity completely. The wet cake was diluted in conc. HCl (1.7 L) and cooled at −5° C. to 0° C. $NaNO_2$ (0.6 Kg) solution in water (2.0 L) was cooled at −5° C. and charged dropwise to the above HCl solution and stirred for 45 min. The reaction mixture was filtered at −5° C.

(ii) Preparation of (VI) and (VII):

A solution of IV (1.0 Kg) in ethanol (15.0 L) was prepared. A solution of KOH (1.8 Kg) in water (6.0 L) was prepared. A portion (70%) of this KOH solution was added directly to the solution of IV at 10° C. The reaction mixture was cooled to 0° C. The diazonium salt solution from step (i) above and the remaining 30% of the KOH solution were added simultaneously dropwise to the above reaction mixture at 0° C. and stirred for 1 hr. The progress of the reaction was monitored on TLC. A solution of glucose (1.7 Kg in 19.0 L of 2N NaOH) was added to it and stirred overnight at room temperature. The product (VI) was not isolated.

After completion of the reaction, activated Zn powder (1.5 Kg) was charged portionwise and stirred for 4-5 hr at room temperature. The Zn powder was activated by treatment with conc. HCl treatment just before use. The reaction mixture was extracted 4 times with Hexane:Toluene (2:1) mixture (20.0 L). The combined organic layer was washed with water (15 L) and brine (15 L). The organic layer was evaporated up to 90% volume. The crude product was purified by filtration through silica gel column to give the title compound (VII) (0.45 Kg)

Yield: 26%; Purity: 90.0% by HPLC

Example 4

Preparation of 2-(2'-hydroxy-5'-methylacryloxypropyl-3-tert-butylphenyl)-5-chloro-2H-benzotriazol (I)

The methacryloyl chloride employed in the final stage of the process is suitably freshly prepared to lower color caused by degradation products of this component. A mixture of methacrylic acid (1.0 Kg), lithium chloride (6.2 gm) and phosphorous trichloride (0.32 L) was stirred for 2 hr at 60° C. and then 30 min at 30° C. DMF (5.5 ml) and Pinch of LiCl were added. After completion of conversion, the reaction mixture was fraction distilled at 30° C.-35° C. (vapour temperature) and at vacuum 50-60 mm to give pure methacryloyl chloride (0.5 Kg). BHT (150 PPM) was added as preservative To a stirred solution of VII (1.0 Kg) in dichloromethane (5.0 L) was added triethylamine (0.4 L) and cooled to 0° C. Methacryloyl chloride (0.164 L) in methylene dichloride (1.0 L) was added slowly to it and stirred for 2 hr at 0° C. and then 24 hr at room temperature. The reaction mixture was acidified with dilute hydrochloric acid and organic layer was separated. The organic layer was washed with water, brine and then evaporated to dryness under reduced pressure to give crude product (1.0 Kg). The crude product was purified by filtration through silica gel column, and then crystallized from methanol to give the title product (I) (0.7 Kg).

Yield: 58.94%; Purity: 99.00% by HPLC

Example 5

Preparation of 4-(benzyloxy)-2-tert-butylphenol (X)

To a stirred solution of t-butyl hydroquinone (1.0 Kg) in 2-methoxy ethanol (2.0 L), was charged $K_2CO_3$ (2.0 Kg) portionwise under nitrogen atmosphere and the mixture refluxed. Benzyl chloride (0.762 L) was added dropwise at reflux temperature and heated further for 1.5 hr. The progress of the reaction was monitored on TLC. The reaction mixture was cooled and added DM Water (6.0 L). The uppermost oily layer was separated, dissolved in ethyl acetate (3.4 L), and washed with DM water (3.4 L×3). The uppermost oily layer was separated, dried over sodium sulfate and evaporated to dryness to give the crude title compound (1.5 Kg). The crude product was employed in the next step without further purification, Crude yield: 97.28%

Example 6

Preparation of 4-(benzyloxy)-2-tert-butyl-6-[(4-methoxy-2-nitrophenyl)diazenyl]phenol (XII)

i) Preparation of Diazonium Salt (XI) Solution

To a stirred solution of conc. HCl (5.85 L) and water (2.0 L) was charged 4-methoxy-2-nitroaniline (3.325 Kg) portionwise. The reaction mixture was heated at 45° C. for 15 min. Orange suspension became peach colored. The reaction mixture was cooled to −5° C. $NaNO_2$ solution (1.4 Kg in 4.2 L water) was charged dropwise to the reaction mixture and stirred at −5° C. for 45 min. The reaction mixture was filtered at −5° C. through Celite™ to remove insoluble impurities.

ii) Preparation of (XII)

To a stirred solution of X (3.12 Kg) in ethanol (36 L) was charged KOH (2.65 Kg in 11.62 L DM Water) solution. The reaction mixture was cooled at −25° C., simultaneously charged with the diazonium salt solution of step (i) and a KOH solution (1.97 Kg in 3.75 L DM Water), added dropwise to the reaction mixture and stirred a further 30 min at −20° C. The brownish red precipitate was separated by filtration and purified by slurry wash with methanol (10 L). The red precipitate was further purified by slurry wash with DM water (20 L) followed by methanol (10 L) slurry wash. The product was dried under reduce pressure at 30° C. for 4-6 hr to give title compound (XII) as a red solid (3.12 Kg).

Yield: 58.5%; Purity: Almost single spot on TLC.

Example 7

Preparation of 4-(benzyloxy)-2-tert-butyl-6-(5-methoxy-2H-1,2,3-benzotriazol-2-yl)phenol (XIII)

To a stirred solution of XII (3.12 Kg) in ethanol (36 L), a glucose solution (2.496 Kg in 15.6 L 2N NaOH) was added dropwise under nitrogen atmosphere. The reaction mixture was stirred at room temperature for 24 hr. Zinc powder (5.46 Kg) previously activated with HCl solution was charged portionwise to the reaction mixture. The reaction mixture was heated at 60° C. for 4 hr to 6 hr until N-Oxide completely consumed. The reaction mixture was cooled and extracted with 15 liters of a 2:1 hexane:toluene mixture. The organic layer was separated and the aq. layer was re-extracted with a 2:1 hexane:toluene mixture (15 L×3). The organic layer was combined and evaporated up to 90% volume. Upon standing at room temperature the organic layer was solidified. The solid was purified by the slurry wash with 5 L of a 95:5 hexane:toluene mixture followed by a methanol slurry wash (3 L) to give title compound (XIII) (1.34 Kg).

Yield: 51.66%; Purity: 70% (by HPLC).

Example 8

Preparation of 2-tert-butyl-6-(5-methoxy-2H-1,2,3-benzotriazol-2-yl)benzene-1,4-diol (XIV)

To a stirred solution of (XIII) (3.1 Kg) in ethanol (52 L), was charged a slurry of 10% Pd/C (300 g in 750 ml water) under nitrogen atmosphere. Formic acid (1.16 L) was added followed by addition of solution of ammonium formate (1.452 Kg) in DM water (755 ml). The reaction mixture was heated at 50° C. for 6 hr. The reaction mixture was cooled to room temperature and filtered. DM Water (31 L) was added to the filtrate, stirred and extracted with toluene (62 L). The organic layer was separated and washed with of (1:1) water: ethanol mixture (31 L). The organic layer was dried on sodium sulfate and evaporated up to 80%. The residual liquid was cooled to 0-5° C., filtered and dried at 50° C. for 1 hr to give the title product (XIV) (1.254 Kg). If required, the product was leached with methanol to obtain required purity.

Yield: 52.05%; Purity: 99% (by HPLC).

Example 9

Preparation of Chloropropyldimethylvinylsilane

To a stirred solution of 1 M vinyl magnesium bromide in THF (9.1 L), 3-chloropropyl dimethylchlorosilane (1.5 Kg) was added over the period of 3 hr through an addition. The reaction mixture stirred further for 2 hr. Added D.M water (9.1 L) and separated the organic layer. The hazy aqueous layer was filtered through hyflo bed and extracted with dichloromethane (3.0 L). The dichloromethane extract was mixed with organic layer and evaporated to dryness to give yellow liquid which was distilled using a Vigreaux column to get pure colorless title product (0.986 Kg)

Yield: 66.49%; Purity: 91.3% (by GC).

Example 10

Preparation of Iodopropyldimethylvinylsilane (X)

To a stirring solution of chloropropyldimethylvinylsilane (645 g) in ethyl methyl ketone (4.65 L), sodium iodide (1.215 Kg) was added under nitrogen and the mixture heated at 75° C. for 24 hr. The reaction mixture was cooled and added D.M. Water (1.62 L) and separated organic layer. The aqueous layer was re-extracted with ethyl methyl ketone (1.16 L) and the extract combined with the organic layer. The organic layer was dried on sodium sulfate and evaporated to dryness. Orange oil was purified by vacuum distillation to give colourless liquid the title product (540 g).

Yield: 53.6%; Purity: 97% (by HPLC).

Example 11

Preparation of 2-[3'-tert-butyl-5'-(3''-dimethylvinylsilylpropoxy)2'-hydroxypheynyl]-5-methoxybenzotriazol (XVI)

To a stirred solution of compound (XIV) (624 g) in ethanol (3.31 L), charged $K_2CO_3$ (937 g) under stirring. Iodopropyldimethylvinylsilane (XV) (530 g) was added and heated the reaction mixture at 75° C. for 12 hr. The reaction mixture was cooled to room temperature and DM Water (3.31 L) was added to it. The reaction mixture was extracted with hexane:toluene (3:1) (3.31 L). The organic layer was separated and washed with 50% aq. ethanol (3.31 L). The organic layer was dried on sodium sulfate and evaporated to dryness to give the product (700 g). The product was purified by crystallization from methanol to give the title compound (XVI) (510 g).

Yield: 58.25%; Purity: 99% (by HPLC).

The above disclosure is intended to be illustrative and not exhaustive. This description will suggest many variations and alternatives to one of ordinary skill in this art. The various elements described above can be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

Lastly, those skilled in the art may recognize other equivalents to the specific embodiment described herein which equivalents are intended to be encompassed by the claims attached hereto.

The invention claimed is:

1. A method of preparing a monomer of formula (E):

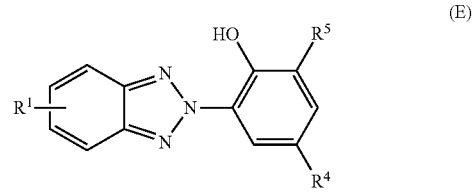

where $R^1$ is H, a halogen atom, alkyl or alkoxy, $R^4$ is a group having a polymerizable C=C double bond and a linking moiety with an ester and/or ether group, and $R^5$ is H, or a straight or branched alkyl of 1-6 carbon atoms, the method comprising:

a) preparing a compound (F)

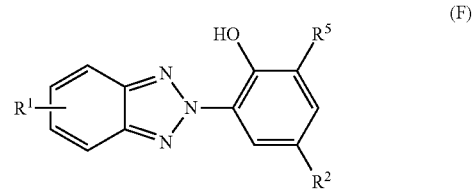

where $R^2$ is OR, and R is an organic leaving group;

b) deprotecting the $R^2$ group of the compound (F) to produce a compound (D):

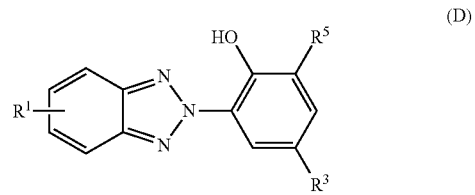

where $R^3$ is OH; and then c) reacting the compound (D) with an alkyl halide substituted with a polymerizable C=C double bond, or a carboxylic acid halide or anhydride having a polymerizable C=C double bond thereon to produce said compound (E).

2. A method as in claim 1 wherein R is an alkaryl group that is optionally substituted on the aromatic ring, a tetrahydropyranyl group that is optionally substituted on the pyrane ring or a t-butyldimethysilyl group.

3. A method as in claim 1 wherein in step c) the compound (D) is reacted with an alkyl halide substituted with a polymerizable C=C double bond.

4. A method as in claim 3 wherein the alkyl halide substituted with a polymerizable C=C double bond is a compound of the formula $X—R^7—R^8$ where X is a labile halogen atom $R^7$ is alkylene and $R^8$ is a silyl group having a vinyl group attached to the silicon atom thereof.

5. A method as in claim 3 wherein the alkyl halide substituted with a polymerizable C=C double bond is an alkyl iodide having polymerizable C=C double bond.

6. A method as in claim 3 wherein the alkyl halide substituted with a polymerizable C=C double bond is a compound of the formula I—$R^7$Si($R^9$)$_2$CH=CH$_2$, where $R^7$ is alkylene and the $R^9$ groups are the same or different monovalent hydrocarbon groups.

* * * * *